United States Patent [19]

Tafani et al.

[11] Patent Number: 5,135,499
[45] Date of Patent: Aug. 4, 1992

[54] DEVICE FOR DELIVERING A PHARMACOLOGICALLY ACTIVE PRINCIPLE BY ELECTROLYTIC PUMPING

[75] Inventors: Jean-Pierre Tafani, Paris; Francis Valter, Chatenay Malabry; Slim Zeghal; Jean Alexandre, both of Paris, all of France

[73] Assignee: Apcis, Reims, France

[21] Appl. No.: 659,409

[22] PCT Filed: Jul. 12, 1990

[86] PCT No.: PCT/FR90/00526
§ 371 Date: Mar. 11, 1991
§ 102(e) Date: Mar. 11, 1991

[87] PCT Pub. No.: WO91/00753
PCT Pub. Date: Jan. 24, 1991

[30] Foreign Application Priority Data

Jul. 12, 1989 [FR] France .................. 89 09391

[51] Int. Cl.[5] .............................. A61M 37/00
[52] U.S. Cl. ...................... 604/141; 604/140
[58] Field of Search .......... 604/141, 145, 140, 151, 604/153, 132, 890.1, 891.1, 892, 93

[56] References Cited

U.S. PATENT DOCUMENTS

| 3,115,280 | 12/1963 | Battista | 222/95 |
| 3,895,538 | 7/1975 | Richter | 604/891.1 |
| 4,715,850 | 12/1987 | Tran | 604/891 X |
| 4,886,514 | 12/1989 | Maget | 604/891.1 |

FOREIGN PATENT DOCUMENTS

| 0209644 | 1/1987 | European Pat. Off. | 604/891.1 |
| 2195461 | 3/1974 | France . | |
| 2305197 | 10/1976 | France . | |

Primary Examiner—John J. Wilson
Assistant Examiner—Jeffrey A. Smith
Attorney, Agent, or Firm—Blakely, Sokoloff, Taylor & Zafman

[57] ABSTRACT

The device includes an electrolysis cell (C) comprising: a closed variable volume first chamber (2) containing an electrolyte that gives off gas under the effect of an electrolysis voltage applied to electrodes (3, 4) in contact with the electrolyte, the gas given off causing the first chamber to expand; and a variable volume second chamber (7) containing the active principle, said second chamber opening out to the outside via an orifice (11) enabling the active principle to be delivered; the total volume of the two chambers (2, 7) being constant, such that expansion of the first chamber causes the volume of the second chamber to be reduced and gives rise to a corresponding controlled expulsion of the active principle contained therein. According to the invention, the two chambers (2, 7) are separated from each other by a flexible wall (6) uniformly subjected to the pressure resulting from gas being given off in such a manner as to reduce the volume of the second chamber (7) and expel the active principle; and the first chamber (2) contains a liquid electrolyte in which the electrodes (3, 4) that extend over the major portion of the length of said first chamber are immersed so that the electrodes are always at least in part in contact with the electrolyte regardless of the position of the device.

10 Claims, 4 Drawing Sheets

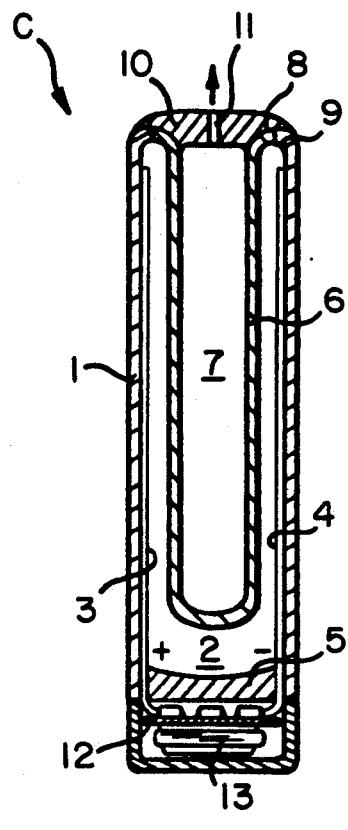
FIG_1
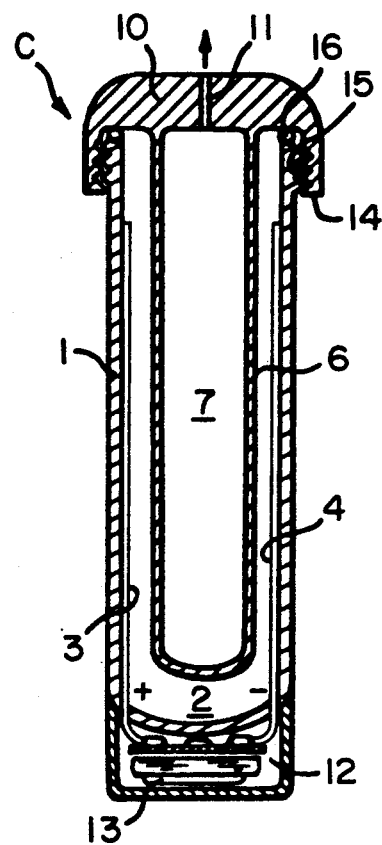
FIG_2
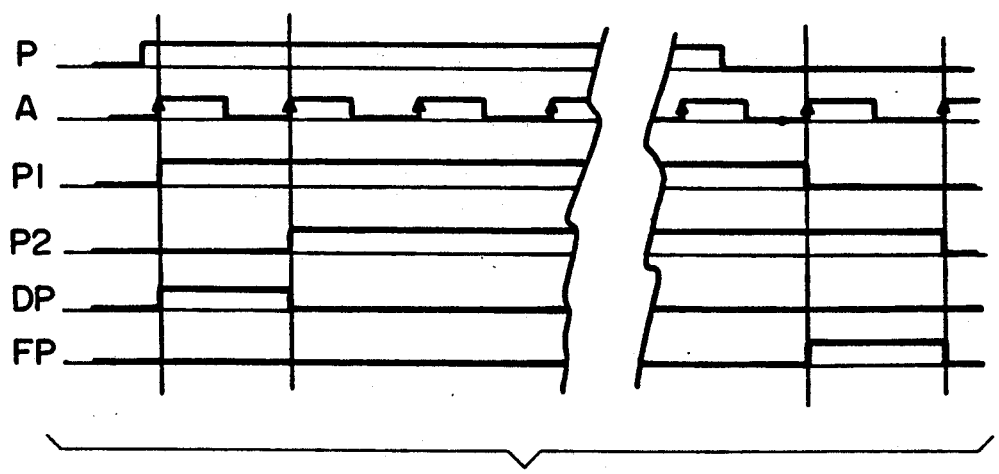
FIG.5

DEVICE FOR DELIVERING A PHARMACOLOGICALLY ACTIVE PRINCIPLE BY ELECTROLYTIC PUMPING

BACKGROUND OF THE INVENTION

1. Field of the Invention

The present invention relates to a device for delivering a pharmacologically active principle by electrolytic pumping.

Such a device is described, for example, in FR-A-2 195 461 which describes, in one of its embodiments, an electrolytic effect pump comprising a closed, variable volume first chamber containing a solid electrolyte (gelled electrolyte) giving off gas under the effect of a voltage applied to a pair of electrodes. The gas given off expands the first chamber which is generally bellows shaped.

The pump also includes a variable volume second chamber containing the active principle and opening out to the outside via an orifice enabling the principle to be dispensed. A rigid vessel defines the total volume of the two chambers, which total volume is constant, such that inflation of the bellows causes a reduction in the volume of the second chamber and corresponding, controlled expulsion of the active principle contained therein.

2. Description of the Prior Art

One of the main difficulties encountered with electrolytic effect pumps of this type is controlling the flow rate of the active principle.

The phenomenon of electrolysis is a process which naturally varies over time, given the gradual changes in the physico-chemical properties both of the electrolyte (in particular its own resistance) and of the electrodes (polarization).

The above-mentioned pump structure is unsuitable for obtaining a flow of active material which is simultaneously exact, accurate, and stable.

In addition, the pump structure proposed in that document is intended essentially for delivering the active principle continuously over relatively long periods of time. By using a solid electrolyte, the time constant of the electrolysis cell is relatively long because of the necessary diffusion through the gell. This electrolytic pump structure is therefore unsuitable for expelling very short spot doses, and a fortiori for expelling doses which are short and accurate.

New active principles such as growth hormone, releasing factor therefor, numerous peptides, hormones, chemical mediators, certain antibiotics, and certain anti-mitotics require discontinuous and frequent injections rather than continuous perfusion of substance at a rate which is fixed and constant over time, for the purpose of conserving their therapeutic effectiveness or for reducing side effects.

The flow rate characteristic of the injected active principle as a function of time must therefore have very narrow peaks which are impossible to achieve if the device has too long a time constant, as would be the case with a solid electrolyte.

In contrast, using a solid electrolyte solves the problem of permanent contact between electrodes and electrolyte since the gas given off by the phenomenon of electrolysis diffuses out from the gell and does not interpose itself between the electrodes and the electrolyte as could happen using a liquid electrolyte (particularly in the context of a device which is implanted or swallowed since at any given moment such a device may have arbitrary orientation in three dimensions).

The present invention seeks to remedy these drawbacks by proposing an electrolytic effect pump whose structure makes it possible to control the flow rate of the active principle extremely accurately, and also to make it highly constant over time.

Another object of the present invention is to propose a structure adapted to sequential injection of spot doses, i.e. doses which are short and accurate (typically for a duration of a few seconds or a few fractions of a second).

Another object of the invention is to provide a device which, by virtue of its specific configuration, is easily implantable or ingestable, so as to enable the active principle to be delivered in situ.

SUMMARY OF THE INVENTION

To this end, the present invention provides a device for delivering a pharmacologically active principle by electrolytic pumping, the device being of the same type as that of above-mentioned FR-A-2 195 461, i.e. comprising: a closed variable volume first chamber containing an electrolyte that gives off gas under the effect of an electrolysis voltage applied to electrodes in contact with the electrolyte, the gas given off causing the first chamber to expand; and a variable volume second chamber containing the active principle, said second chamber opening out to the outside via an orifice enabling the active principle to be delivered; the total volume of the two chambers being constant, such that expansion of the volume of the first chamber causes the volume of the second chamber to be reduced and gives rise to a corresponding controlled expulsion of the active principle contained therein.

According to the invention, this device is characterized in that the two chambers are separated from each other by a flexible wall uniformly subjected to the pressure resulting from gas being given off in such a manner as to reduce the volume of the second chamber and expel the active principle; and the first chamber contains a liquid electrolyte in which the electrodes that extend over the major portion of the length of said first chamber are immersed so that the electrodes are always at least in part in contact with the electrolyte regardless of the position of the device.

In a preferred embodiment, the first chamber is defined by a rigid tube closed at one of its ends, the tube containing a central flexible bag extending axially over the major portion of the length of the tube and defining the second chamber, the rim of the bag being connected to the rigid tube at its end opposite to its closed end and being closed by a plug including the orifice through which the active principle is delivered.

In this case, the electrodes are preferably elongate electrodes disposed against the inside wall of the tube and extending over the major portion of the length thereof. Preferably, several similar pairs of electrodes are then provided distributed circumferentially in regular manner against the inside wall of the tube with electrode polarity alternating from one electrode to the next.

Preferably a resistor is provided in series in the electrolysis cell circuit, the resistance of the resistor being significantly higher than the resistance of the electrolyte as measured between the electrodes.

The invention also proposes applying the electrolysis voltage to the electrodes intermittently, so as to deliver the active principle in predetermined repeated doses that are administered at regular intervals.

To this end, the device of the invention then includes an electrolysis control circuit comprising: a source of electrolysis voltage; an oscillator delivering a predetermined reference frequency; first counter means receiving the reference frequency at an input and delivering a periodic sequencing signal at an output defining the periodicity with which a dose of the active principle is administered; second counter means receiving the reference frequency at an input and delivering a periodic activation signal at an output defining the length of time during which each dose of active principle is administered; and a control circuit combining the sequencing signal and the activation signal in such a manner as to selectively control application of the electrolysis voltage to the terminals of the electrolysis cell so as to cause the active principles to be delivered with the desired periodicity and for the desired length of time.

The electrolysis control circuit may further include third counter means receiving the reference frequency at an input and delivering an inhibit signal at an output, the inhibit signal corresponding to the end of administering any active principle, the control circuit preventing any application of an electrolysis voltage after the inhibit signal has appeared.

In the device of the invention, the second chamber may be modified in such a manner as to eject a plurality of active principles and the set of pairs of chambers combined with a single control system can then be used to inject two active principles or groups of active principles alternately or simultaneously.

BRIEF DESCRIPTION OF THE DRAWINGS

An embodiment of the invention is now described by way of example with reference to the accompanying figures, in which:

FIG. 1 is a section through an embodiment of an electrolytic pump of the invention;

FIG. 2 shows a variant of the FIG. 1 embodiment;

FIG. 5 is a set of timing diagrams corresponding to various signals produced by the circuits of FIGS. 3 and 4.

DETAILED DESCRIPTION OF THE INVENTION

Figure 3:
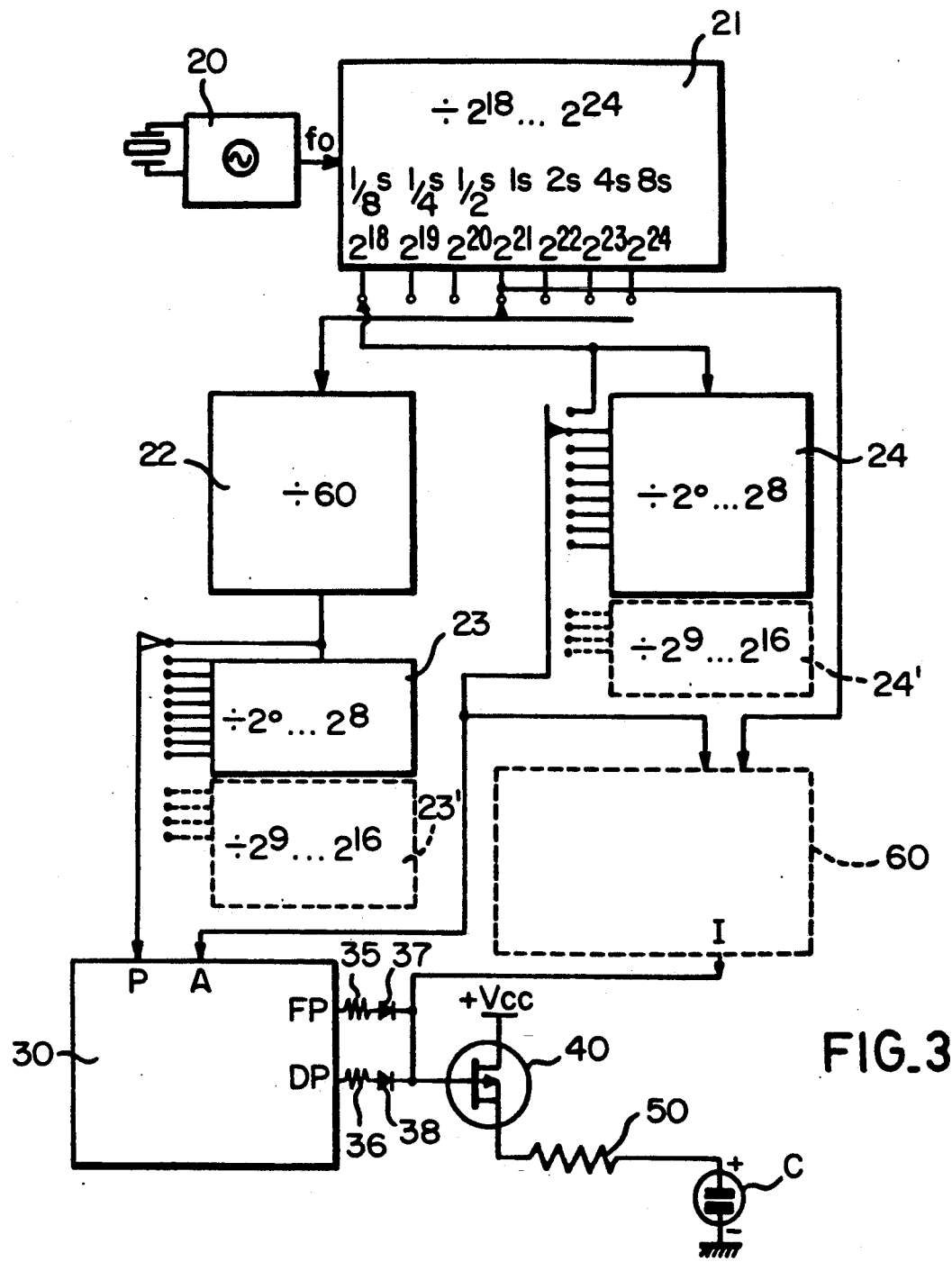
FIG. 3 is a block diagram of the control circuit for the pump of FIGS. 1 and 2.

FIG. 1 shows the general structure of the electrolytic effect pump of the invention.

This pump essentially comprises a rigid outer tubular vessel 1 defining a first chamber 2 containing a liquid electrolyte (it should be observed that it is important for the electrolyte to be liquid if spot doses are to be injectable with a very short response time). This outer vessel 1 is made of biocompatible material (e.g. silicone resin) if the device is to be implanted or ingested, as will generally be the case.

Electrodes 3 and 4 are placed against the wall of the outer vessel 1 and are advantageously in the form of elongate wires, e.g. copper wires (or any other suitable metal, given the nature of the electrolyte), which wires extend over substantially the entire length of the tube 1. In addition, several pairs of electrodes are provided (a single pair of electrodes 3, 4 being visible in the section of FIG. 1), all of which are disposed in parallel against the wall of the tube 2 and are uniformly distributed around the circumference thereof with alternating polarities from one electrode to the next.

This particular configuration makes it possible to be sure that there will always be at least one pair of electrodes that is at least partially immersed in the liquid regardless of the amount of gas given off and regardless of the orientation in three dimensions of the device (which is essential for a device which is implanted or ingested).

It is thus possible to provide two, four, six, or eight electrodes (or even more), thus ensuring that there will be permanent electrode/electrolyte contact and that this contact will take place over sufficient electrode area.

It can also be seen that this particular electrode configuration avoids having any dead volume inside the electrolysis cell, thus making it possible to have a very high ratio of active principle volume over device volume, thus making it possible to reduce the overall dimensions of the device to a minimum (which constitutes an essential characteristic for a device which is intended to be implanted or ingested).

The tube 1 containing the electrolyte is closed at one of its ends (bottom end 5 in the orientation shown in FIG. 1) and it receives a flexible bag 6 in its center over the major portion of its length, the bag defining a second chamber 7 which encloses the active principle.

The bag 6 is in the form of a glove finger and it is made of a deformable material (e.g. an elastomer) which is chemically inert both relative to the electrolyte and relative to the active principle, and it is impermeable to the gas (hydrogen) given off by the electrolysis phenomenon.

At its open end, the second chamber 7 has a rim 8 which is connected in gastight manner (e.g. by gluing) to the corresponding rim 9 of the rigid outer tube 1, thereby completely closing the volume of the first chamber 2.

The second chamber 7 is closed by an element 10 provided with a capillary 11 for ejecting the active principle (in a variant the capillary 11 could be replaced by a tube for delivering the substance to a point at a distance from the pump).

Finally, the device includes an electrical control circuit 12, described below, which is powered by a battery 13 which serves as a source of energy for the electrolysis. Advantageously, the electrical components 12 and 13 are disposed at one of the ends of the tube, as shown in the figure.

It may also be observed that because of the very large area of the flexible wall 6, the active principle is compressed uniformly and isostatically with very low mechanical resistance to transmitting the pressure of the gas produced in the first chamber 2 to the active principle contained in the second chamber 7. As a result, pressure peaks produced by appropriate control of the electrolysis are faithfully transmitted to the volume of active principle and are converted into peaks in the flow of active principle expelled via the capillary 11.

FIG. 2 shows a variant embodiment in which the flexible bag 6 and the plug 10 are formed integrally by an item in the form of screw plug with tapping 14 for engaging on threads 15 of the outer tube 1, and with sealing being provided by an O-ring 16. The other items are similar to those shown in FIG. 1 and are designated by the same reference numerals.

This modified configuration makes the cell easily reusable merely by unscrewing the item 10, thereby enabling used electrolysis solution to be exchanged for new solution, with the pocket 6 being recharged with a new quantity of active principle by injection through the capillary 11.

Figure 6:
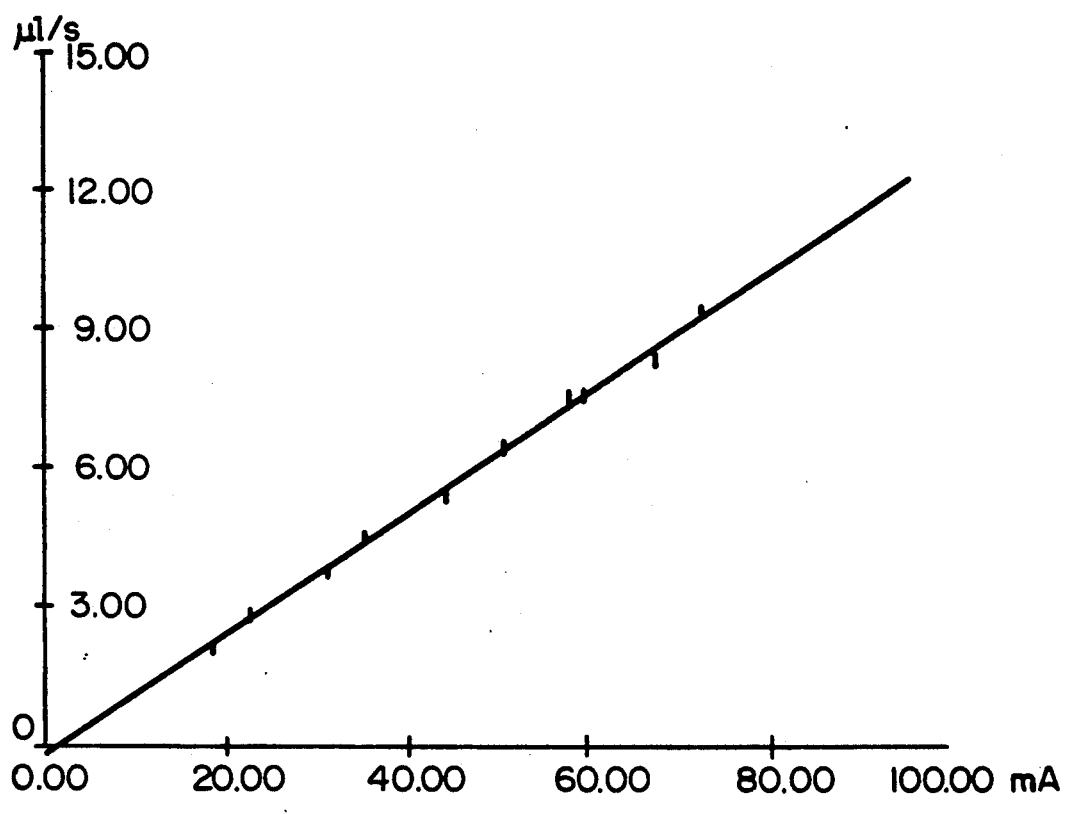
FIG. 6 is a graph showing the characteristic obtained from a cell of the type illustrated in FIG. 1, with volume flow rate plotted as a function of current flow through the electrolysis cell.

In a third alternate embodiment of the present invention, as shown in FIG. 6, the device is modified such that a variable volume third chamber 80 having a third orifice 81 and a variable volume fourth chamber 82 having a fourth orifice 83 are disposed within the closed variable volume first chamber 2. By use of this configuration, the volumes of both of the variable volume third and fourth chambers 80,82 are simultaneously reduced when the volume of the closed variable volume first chamber 2 expands due to the gas given off therein. The device is thereby able to eject two active principles either simultaneously or alternatively by means of the same control circuit.

Figure 7:
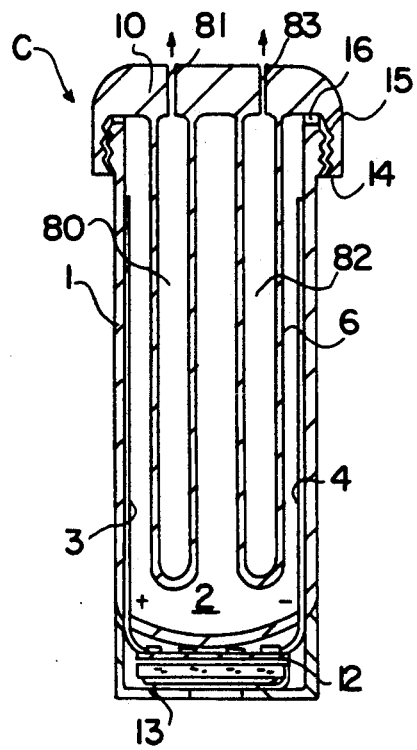
FIG. 7 is a third alternate embodiment of the present invention showing a plurality variable volume chambers within the closed variable volume first chamber of the device.
Figure 8:
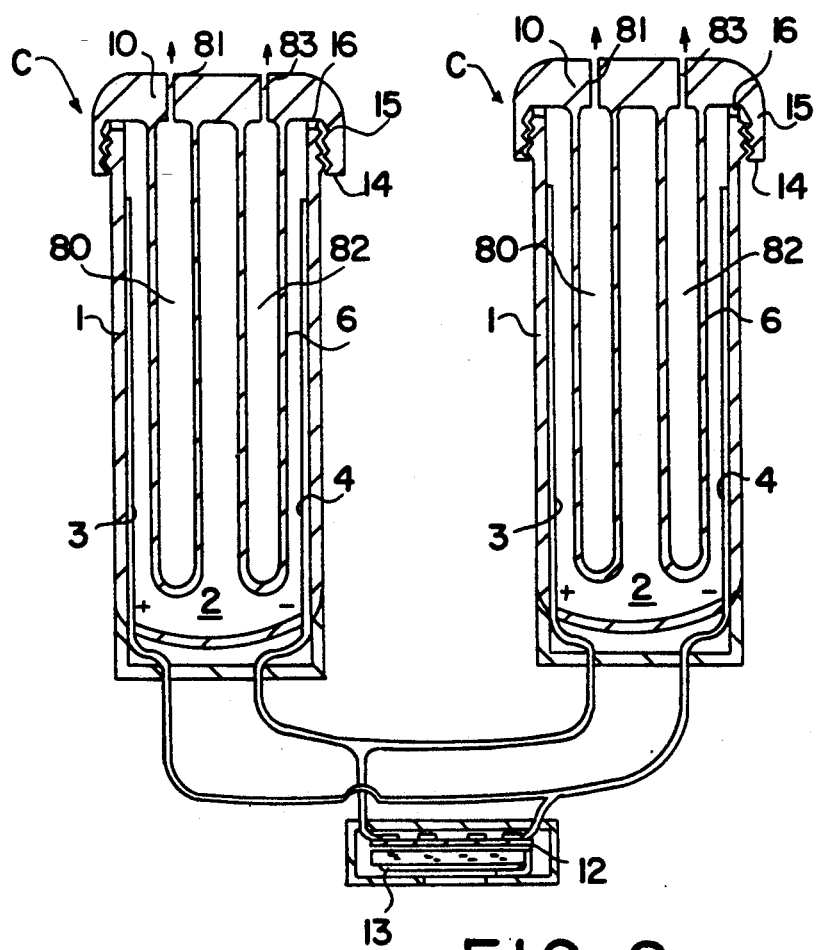
FIG. 8 is a fourth alternate embodiment of the invention showing a plurality of the devices in common with a single control circuit.

In a fourth alternate embodiment of the present invention, as shown in FIG. 7, the invention is further improved by placing two of the delivery devices, as modified above in the third alternate embodiment, in common with a single control circuit so that groups of different active principles can be ejected either simultaneously or alternatively by separate devices by use of one control circuit.

FIG. 3 shows the control circuit for obtaining sequential injections of short controlled doses of active principle.

The circuit essentially comprises a crystal oscillator 20 delivering a reference frequency $f_o$, e.g. at 2.097 MHz. This reference frequency is applied to a divider circuit 21 which may be set to divide by a number in the range $2^{18}$ to $2^{24}$, thus giving periods lying between $\frac{1}{8}$th of a second and 8 seconds.

A first set of circuits 22, 23, 23' serves to generate a signal P (called the "period signal") defining the periodicity of substance ejection, i.e. the time interval between two successive ejections. These circuits include a divide-by-60 circuit referenced 22 in cascade with a divider which is programmable to divide by a number in the range 1 to $2^8$. If a signal of period 1 s is applied to the input of the divider 22, it is thus possible to obtain period signals P at the output from the divider 23 lying in the range 7.5 s to 3448 min (57 h 28 min).

If so desired, the durations can be further increased by providing a second circuit 23' identical to the circuit 23, thereby making it possible to obtain divisions by numbers lying in the range $2^9$ to $2^{16}$.

In addition to the signal P defining ejection periodicity, it is also necessary to provide a signal A (called the "activation signal") defining the duration specific to each ejection. The activation signal A is obtained from a divider 24 programmable to divide by a number in the range 1 to $2^8$, and receiving pulses of period $\frac{1}{8}$th of a second output from the divider 21, and thus delivering a signal A constituted by a pulse of duration lying in the range $\frac{1}{8}$th of a second to 2048 s (34 min, 8 s). Like the period signal, the duration of the activation signal may be extended by providing an additional divider stage 24' identical to the stage 24 and in cascade therewith.

The period signal P and the activation signal A are applied together to a circuit 30 which combines them to deliver two signals, "an end of period" signal FP and a "beginning of period" signal DP which take turns in controlling activation of the electrolysis cell. To satisfy the ejection periodicity as laid down, it is necessary to control the electrolytic cell not as a function of the state of the period signal P, but as a function of its changes in state: the signal DP thus corresponds to a rising edge and the signal FP to a falling edge, and each of these signals should cause the electrolytic cell to be activated.

Figure 4:
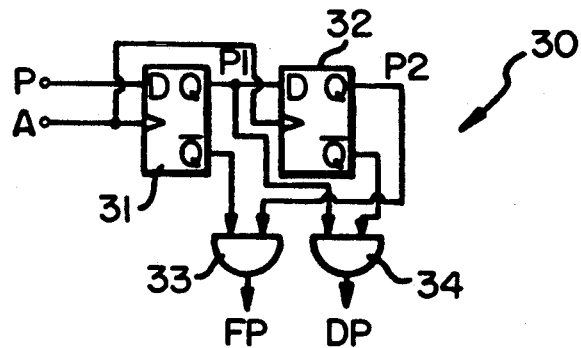
FIG. 4 is a detail of one of the subassemblies of said circuit.

FIG. 4 shows a detail of the control circuit 30. This detail comprises two D-type flip-flops 31 and 32 which receive the activation signal A as their clock signal. The period signal P is applied to the D input of the first flip-flop 31 whose Q output gives a signal $P_1$ which is applied in turn to the D input of the second flip-flop 32 which delivers a signal $P_2$ at its Q output. The respective output signals Q and $\bar{Q}$ from each of the two flip-flops 31 and 32 are combined in the manner shown by two AND gates 33 and 34 to give the signals FP and DP which then control activation of the electrolysis cell.

The timing diagram of FIG. 5 shows the succession of the various signals produced by this control signal 30.

The signals FP and DP are applied via resistors 35 and 36 and diodes 37 and 38 (thus together constituting the equivalent of an OR gate) to the base of a power transistor 40 whose source is connected to the power supply voltage $+Vcc$ and whose drain is connected to one of the electrodes (or to one of the series of electrodes in the pair of electrodes) of the electrolytic cell C via a resistor 50.

The resistance of the resistor 50 is considerably higher than the resistance of the electrolyte, e.g. it may be about 200 ohms, thereby eliminating the effect of the electrolytic cell's own resistance which varies over time because of the changing composition of its electrolyte and because of the polarization of its electrodes.

This makes it possible to stabilize the electrolysis current in spite of changes in the physico-chemical characteristics specific to the electrolytic cell, thereby making it possible to maintain constant electrolysis current whenever electrical feed is applied to the electrolysis cell, thereby ensuring a constant ejection rate of the active principle even after a very long period of operation.

It is preferable for the control electronics to include an inhibit circuit 60 which serves after a predetermined length of time to prevent any further activation of the electrolysis cell, thereby putting a final end to the dispensing of active principle.

The circuit 60 may be a divider circuit operating as a down counter and receiving at its input either pulses delivered at the output of the circuit 21 (when it is desired to stop the pump after a predetermined fixed operating period), or else from the activation signal (when it is desired to stop the pump after it has delivered a predetermined number of spot doses). Once the initially fixed threshold has been reached, the circuit 60 may, for example, deliver a low level inhibit signal I which corresponds to permanently grounding the base of transistor 40, thus inhibiting any subsequent activation of the electrolysis cell (with the signals FP and DP having no further effect).

In a variant, it is also possible to achieve inhibition by short circuiting the battery and this is a better solution from the safety point of view but it prevents the battery being reused if it is desired to recover and reuse the device.

It is also possible to select a battery such that the total energy it is capable of delivering is slightly less than the total energy required for removing all of the active principle contained in the deformable chamber 7.

This prevents electrolysis continuing even after all of the substance has been expelled, which would give rise to severe risks due to excess hydrogen being given off and to the pressure inside the device being raised correspondingly too high.

In order to reduce the energy consumption of the control electronics to a minimum, it is implemented using CMOS circuits together with a MOSFET power transistor, suitable for being controlled directly by CMOS logic.

Naturally the control circuits are not limited to being implemented in the form of hard-wired discrete circuits as shown. It could equally well be implemented in the form of a single hard-wired logic chip, or even as a microprogrammed logic chip. If programmed, it is possible, in particular, to make use of programs (in ROM, EPROM, or EEPROM) to define the selected sequencing and also to enable certain values of essential parameters to be modified and adapted as a function of requirements.

It may also be observed that the system could be initialized and triggered by remote control from external equipment, in a manner known per se.

FIG. 6 shows experimental results for the characteristic of active principle flow rate (in μl/s) as a function of electrolysis current (in mA). The active principle was gentamycine in solution in water at a concentration of 2 kg/l.

It may be observed that excellent linearity is obtained and that it is thus possible to adjust the ejection flow rate of the active principle accurately by controlling the electrolysis current (i.e. by adjusting the series resistor 50).

In addition to the very good correlation between flow rate and current under all circumstances, experiments have also shown that for a given current, very similar flow rate values are obtained for active principles having very different viscosities, which makes it possible to envisage use with active principles having a wide variety of natures.

We claim:

1. A device for delivering a pharmacologically active principle by electrolytic pumping, the device including an electrolysis cell (C) comprising:
   a closed variable volume first chamber (2) containing a liquid electrolyte that gives off gas under the effect of an electrolysis voltage applied to a pair of electrodes (3, 4) in contact with the electrolyte, the gas given off causing the first chamber to expand; and
   a variable volume second chamber (7), said second chamber opening out to the outside of said second chamber via an orifice (11) enabling the active principle to be delivered;
   the total volume of the two chambers (2, 7) being constant, such that expansion of the first chamber causes the volume of the second chamber to be reduced and gives rise to a corresponding controlled expulsion of the active principle contained therein;
   the two chambers (2, 7) are separated from each other by a flexible wall (6) uniformly subjected to the pressure resulting from the gas being given off in such a manner as to reduce the volume of the second chamber (7) and expel the active principle; and
   the first chamber (2) contains the liquid electrolyte in which the pair of electrodes (3, 4) that extend over a major portion of the length of said first chamber are immersed in said liquid electrolyte so that the pair of electrodes are always at least in part in contact with the liquid electrolyte regardless of the position of the device.

2. The device of claim 1, in which the first chamber (2) is defined by a rigid tube (1) closed at a first end (5), the flexible wall of the tube forming a central flexible bag extending axially over a major portion of the length of the tube and defining the second chamber (7), with a rim of the bag being connected to the rigid tube at a second end (9) opposite to its closed end and being closed by a plug (10) including the orifice (11) through which the active principle is delivered.

3. The device of claim 2, in which the pair of electrodes (3, 4) are a pair of elongate electrodes disposed against an inside wall of the rigid tube (1) and extending over the major portion of the length thereof.

4. The device of claim 3, including a plurality of similar pairs of electrodes (3, 4) distributed circumferentially in pairs against the inside wall of the tube (1) with electrode polarity alternating from one electrode to the next.

5. The device of claim 1, including a resistor (50) in series with the electrolysis cell, the resistance of the resistor being significantly higher than the resistance of the electrolyte as measured between the electrodes.

6. The device of claim 1, in which the electrolysis voltage is applied to the electrodes intermittently so as to deliver the active principle in repeated predetermined doses which are administered at regular intervals.

7. The device of claim 6, including an electrolysis control circuit comprising:
   a source of electrolysis voltage (+Vcc);
   an oscillator (20) delivering a predetermined reference frequency;
   first counter means (21, 22, 23) receiving the predetermined reference frequency (fo) at a first input and delivering a periodic sequencing signal (P) at a first output defining a desired periodicity with which a dose of the active principle is administered;
   second counter means (21, 24) receiving the predetermined reference frequency (fo) at a second input and delivering a periodic activation signal (A) at a second output defining a desired length of time during which each of the repeated predetermined doses of the active principle is administered; and
   a voltage control circuit (30–40) combining the periodic sequencing signal and the periodic activation signal in such a manner as to selectively control application of the electrolysis voltage (+Vcc) to the electrolysis cell (C) so as to cause the active principle to be delivered with the desired periodicity and for the desired length of time.

8. The device of claim 7, in which the electrolysis control circuit further includes a third counter means (21, 60) receiving the predetermined reference frequency (fo) at a third input and delivering an inhibit signal (I) at a third output, the inhibit signal corresponding to an end of administering any active principle, the voltage control circuit (30-40) preventing any application of the electrolysis voltage after the inhibit signal has appeared.

9. The device according to any one of claims 1 to 8, characterized in that the second chamber (7) comprises a first compartment having a first orifice and a second compartment having a second orifice, with each of the first and second orifices being capable of delivering the active principle.

10. The device according to claim 9, in which the electrolysis control circuit is common to two of the delivery devices for the purpose of enabling different active principles to be delivered alternately.

* * * * *